United States Patent
Budd et al.

(10) Patent No.: US 6,728,562 B1
(45) Date of Patent: Apr. 27, 2004

(54) METHOD FOR CREATING A VIRTUAL ELECTROGRAM

(75) Inventors: Jeffrey Robert Budd, St. Paul, MN (US); Graydon Ernest Beatty, St. Paul, MN (US); John Anderson Hauck, Shoreview, MN (US)

(73) Assignee: Endocardial Solutions, Inc., St. Paul, MN (US)

( * ) Notice: Subject to any disclaimer, the term of this patent is extended or adjusted under 35 U.S.C. 154(b) by 0 days.

(21) Appl. No.: 09/547,464

(22) Filed: Apr. 12, 2000

Related U.S. Application Data

(63) Continuation of application No. 09/005,105, filed on Jan. 9, 1998, now abandoned, which is a division of application No. 08/387,832, filed on May 26, 1995, now Pat. No. 6,240,307, which is a continuation-in-part of application No. 07/950,448, filed on Sep. 23, 1992, now Pat. No. 5,297,549, and a continuation-in-part of application No. 07/949,690, filed on Sep. 23, 1992, now Pat. No. 5,311,866.

(51) Int. Cl.[7] .............................. A61B 5/04; A61B 5/05
(52) U.S. Cl. ........................................ 600/374; 600/547
(58) Field of Search ................................. 600/374, 382, 600/393, 508, 547; 128/898, 899; 607/122

(56) References Cited

U.S. PATENT DOCUMENTS

| | | | |
|---|---|---|---|
| 5,391,199 A | * | 2/1995 | Ben-Haim .................. 607/122 |
| 5,553,611 A | * | 9/1996 | Budd et al. ................. 600/374 |
| 5,662,108 A | * | 9/1997 | Budd et al. ................. 600/374 |
| 5,697,377 A | * | 12/1997 | Wittkampf .................. 128/899 |

* cited by examiner

Primary Examiner—Max F. Hindenburg
Assistant Examiner—David J. McCrosky
(74) Attorney, Agent, or Firm—Beck & Tysver, P.L.L.C.

(57) ABSTRACT

A mapping catheter is positioned in a heart chamber, and active electrode sites are activated to impose an electric field within the chamber. The blood volume and wall motion modulates the electric field, which is detected by passive electrode sites on the preferred catheter. Electrophysiology measurements, as well as geometry measurements, are taken from the passive electrodes and used to display a map of intrinsic heart activity.

7 Claims, 17 Drawing Sheets

METHOD FOR CREATING A VIRTUAL ELECTROGRAM

CROSS REFERENCED TO RELATED CASES

This application is a continuation of Ser. No. 09/005,105, filed Jan. 9, 1998, now abandoned which is a divisional application of Ser. No. 08/387,832, filed May 26, 1995, now U.S. Pat. No. 6,240,307 which is a national stage application of PCT/US93/09015, filed Sep. 23, 1992, which is a continuation-in-part of U.S. Ser. No. 07/950,448, filed Sep. 23, 1992, now U.S. Pat. No. 5,297,549 and U.S. Ser. No. 07/949,690, filed Sep. 23, 1992, now U.S. Pat. No. 5,311,866. Applicants claim priority to: 08/387,832, filed May 26, 1995, now U.S. Pat. No. 6,240,307; Ser. No. 08/376,067 filed Aug. 20, 1995, now U.S. Pat. No. 5,553,611; and Ser. No. 08/178,128 filed Jan. 6, 1994, now abandoned.

FIELD OF THE INVENTION

The parent invention relates to electrophysiology apparatus which is used to measure and to visualize electrical activity occurring in a patient's heart. The system can display both a visual map of the underlying electrical activity originating in a chamber of a patient's heart and the location of a therapy catheter located within a heart chamber. The electrophysiology apparatus includes several subsystems including: a therapy catheter system, a measurement catheter system and a computer based signal acquisition, control and display system.

BACKGROUND OF THE INVENTION

Many cardiac tachyarrhythmias are caused by conduction defects which interfere with the normal propagation of electrical signals in a patient's heart. These arrhythmias may be treated electrically, pharmacologically or surgically. The optimal therapeutic approach to treat a particular tachyarrhythmia depends upon the nature and location of the underlying conduction defect. For this reason electrophysiologic mapping is used to explore the electrical activity of the heart during a tachyarrhythmic episode. The typical electrophysiologic mapping procedure involves positioning an electrode system within the heart. Electrical measurements are made which reveal the electrical propagation of activity in the heart. If ablation is the indicated therapy then a therapy catheter is positioned at the desired location within the heart and energy is delivered to the therapy catheter to ablate the tissue.

There are numerous problems associated with these electrophysiologic diagnostic and therapeutic procedures. First the testing goes on within a beating heart. The motion of the diagnostic catheter and treatment catheter can injure the heart and provoke bouts of arrhythmia which interfere with the collection of diagnostic information. During the delivery of ablation therapy it is common to use fluoroscopic equipment to visualize the location of the catheters. Many physicians are concerned about routine occupational exposure to X-rays. In addition, the traditional mapping techniques do not provide a high resolution view of the electrical activity of the heart which makes it difficult to precisely locate the source of the arrhythmia.

SUMMARY

The electrophysiology apparatus of the invention is partitioned into several interconnected subsystems. The measurement catheter system introduces a modulated electric field into the heart chamber. The blood volume and the moving heart wall surface modify the applied electric field. Electrode sites within the heart chamber passively monitor the modifications to the field and a dynamic representation of the location of the interior wall of the heart is developed for display to the physician. Electrophysiologic signals generated by the heart itself are also measured at electrode sites within the heart and these signals are low pass filtered and displayed along with the dynamic wall representation. This composite dynamic electrophysiologic map may be displayed and used to diagnose the underlying arrhythmia.

A therapy catheter system can also be introduced into the heart chamber. A modulated electrical field delivered to an electrode on this therapy catheter can be used to show the location of the therapy catheter within the heart. The therapy catheter location can be displayed on the dynamic electrophysiologic map in real time along with the other diagnostic information. Thus the therapy catheter location can be displayed along with the intrinsic or provoked electrical activity of the heart to show the relative position of the therapy catheter tip to the electrical activity originating within the heart itself. Consequently the dynamic electrophysiology map can be used by the physician to guide the therapy catheter to any desired location within the heart.

The dynamic electrophysiologic map is produced in a step-wise process. First, the interior shape of the heart is determined. This information is derived from a sequence of geometric measurements related to the modulation of the applied electric field. Knowledge of the dynamic shape of the heart is used to generate a representation of the interior surface of the heart.

Next, the intrinsic electrical activity of the heart is measured. The signals of physiologic origin are passively detected and processed such that the magnitude of the potentials on the wall surface may be displayed on the wall surface representation. The measured electrical activity may be displayed on the wall surface representation in any of a variety of formats. Finally, a location current may be delivered to a therapy catheter within the same chamber. The potential sensed from this current may be processed to determine the relative or absolute location of the therapy catheter within the chamber.

These various processes can occur sequentially or simultaneously several hundred times a second to give a continuous image of heart activity and the location of the therapy device.

BRIEF DESCRIPTION OF THE DRAWINGS

An exemplary and illustrative form of the invention is shown in the drawings and identical reference numerals refer to equivalent structure throughout.

DETAILED DESCRIPTION

Figure 1:
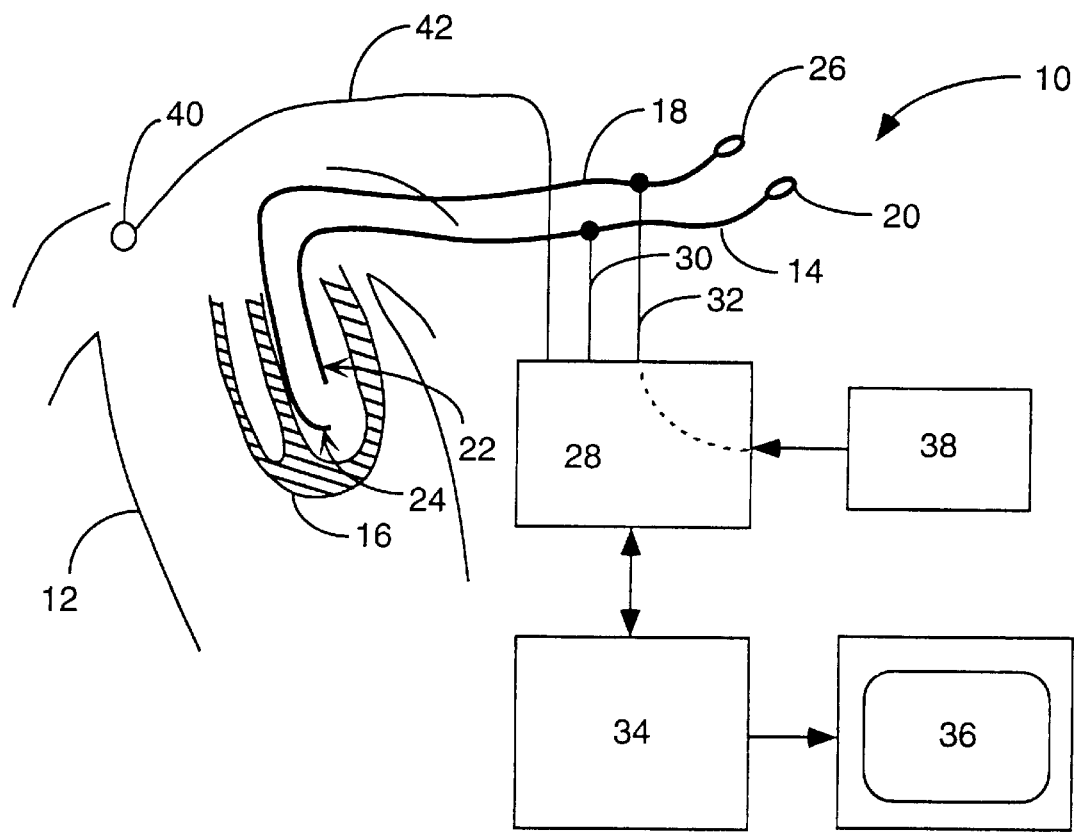
FIG. 1 is a schematic block diagram of the electrophysiology apparatus.

FIG. 1 shows the electrophysiologic apparatus 10 connected to a patient 12. In a typical procedure a monitoring catheter system 14 is placed in the heart 16 to generate a display of the electrical activity of the heart 16. After diagnosis a therapy catheter 18 may be inserted into the heart to perform ablation or other corrective treatment.

The monitoring catheter 14 has a proximal end 20 which may be manipulated by the attending physician, and a distal end 22 which carries a monitoring catheter electrode set 44. In general the distal end 22 of the monitoring catheter 14 will be relatively small and will float freely in the heart chamber. The therapy catheter 18 has a distal end 24 which carries a therapy catheter electrode set 46. The therapy catheter also has proximal end 26 which can be manipulated by the attending physician.

The electrode sets located on the catheters are coupled to an interface system 28, through appropriate cables. The cable 30 connects the monitoring catheter electrode set 44 to the interface system 28 while cable 32 connects the therapy catheter electrode set 46 to the interface system 28. The interface system 28 contains a number of subsystems which are controlled by a computer 34. The data collected by the interface system 28 is manipulated by the computer 34 and displayed on a display device 36. Surface electrodes represented by electrode 40 may also be coupled to the electrophysiology apparatus 10 for several purposes via an appropriate cable 42. A therapy generator 38 is connected to the therapy catheter electrode 60 and to the therapy surface ground 70, through the interface system 28. The skin surface electrode cable 42 couples the ECG surface electrodes 74 to the ECG system 39, which may be a subsystem of interface system 28.

Figure 2:
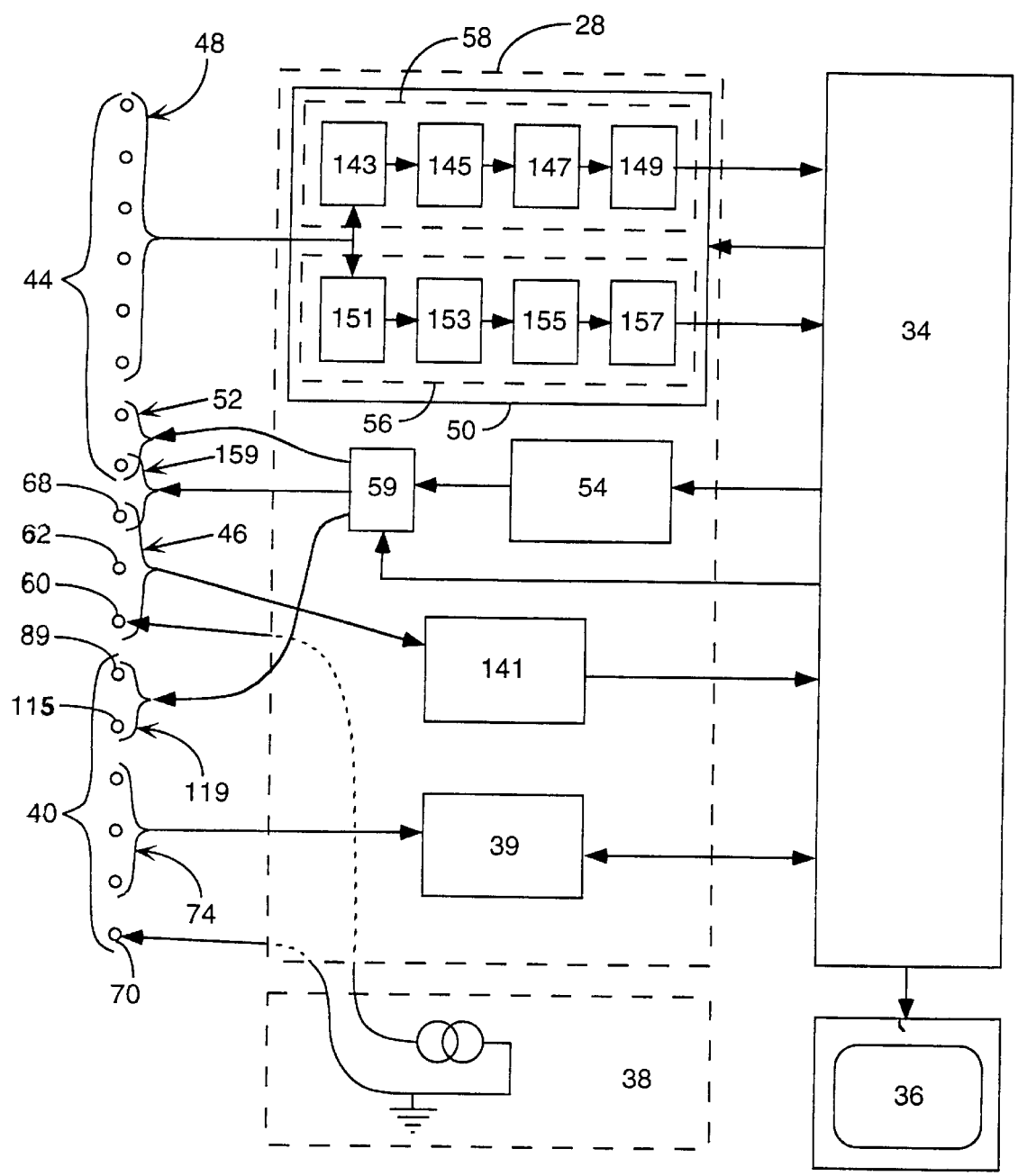
FIG. 2 is a block diagram representing the partitioning of the electrophysiology apparatus.

FIG. 2 is a schematic diagram showing an illustrative segmentation of the electrode sets and their electrical connections to subsystems in the electrophysiology apparatus 10. For example the monitoring electrode set 44 contains a subset of passive electrodes 48 which are connected to a signal conditioner 50. The monitoring electrode set 44 also contains a subset of active electrodes 52 which are connected to a signal generator 54 through a switch 59. The signal generator 54 is controlled by the computer 34. In operation, the signal generator 54 generates a burst of (4800 Hz for example) signals which are supplied to the active electrode set 52. This energy sets up an electric field within the heart 16 chamber. The electrical potentials present on the passive electrode set 48 represent the summation of the underlying electrophysiological signals generated by the heart and the field induced by the burst. The signal conditioner 50 separates these two components. The preferred technique is to separate the signals based upon their frequency.

The high pass section 56 of the signal conditioner extracts the induced field signals as modulated by the blood volume and the changing position of the chamber walls 125. First, the signals are amplified with a gain of approximately 500 from passive electrodes 48 with amplifier 151. Next, the signals are high pass filtered at roughly 1200 Hz by filter 153. Then the 4800 Hz signal is extracted by demodulator 155. Finally, the individual signals are converted to digital format by the analog to digital converter 157 before being sent to the computer 34.

The low pass section 58 of the signal conditioner 50 extracts physiologic signals. First, signal drift is reduced with a 0.01 Hz high pass filter 143. Next, a programmable gain amplifier 145 amplifies the signals. Then a low pass filter 147 removes extraneous high frequency noise and the signal from the induced field. Finally, the physiologic signals are converted to digital format by the analog to digital converter 149 before being sent to the computer 34.

The therapy catheter electrode set 46 includes at least one therapy delivery electrode 60, and preferably one or more monitoring electrodes 62, and one or more locator electrodes 68. The therapy delivery electrode 60 cooperates with the ground electrode 70, which is generally a skin patch electrode, to deliver ablation energy to the heart. These electrodes are coupled to the ablation energy generator 38 which is shown as an RF current source. A locator electrode 68 is provided which is preferably proximate the delivery electrode 60, but can be a separate electrode site located near the distal end 24 of the therapy catheter 18. This electrode site is coupled with an active electrode 52 through a switch 59 to the signal generator 54. In use, the electric field coupled to the therapy catheter 18 permits the physician to track and visualize the location of the locator electrode 68 on the display device 36. The therapy catheter electrode set 46 can also be used to monitor the physiologic signals generated at the chamber wall 125 by a low pass signal conditioner 141 which is similar to the low pass section 58 of the signal conditioner 50. These digitized signals are then sent to the computer 34.

At least one electrode pair 119 of surface electrodes 40 are also coupled to the signal generator 54 through switch 59. Each electrode 89 and 115 are placed opposite each other on the body surface with the heart 16 in-between them. The induced field is sensed by passive electrodes 48 and conditioned by the high pass section 56 of the signal conditioner 50. This field helps the computer 34 align or orient the passive electrodes 48 to the body for better visualization of the heart on the monitor 36.

The ECG subsystem 39 accepts signals from standard ECG skin electrodes 74. It also contains a low pass section similar to the low pass section 58 of signal conditioner 50. In general, the passive electrode set 48 and active electrode set 52 will reside on a single catheter, however it should be recognized that other locations and geometries are suitable as well. Both basket and balloon devices are particularly well suited to this application.

Figure 3:
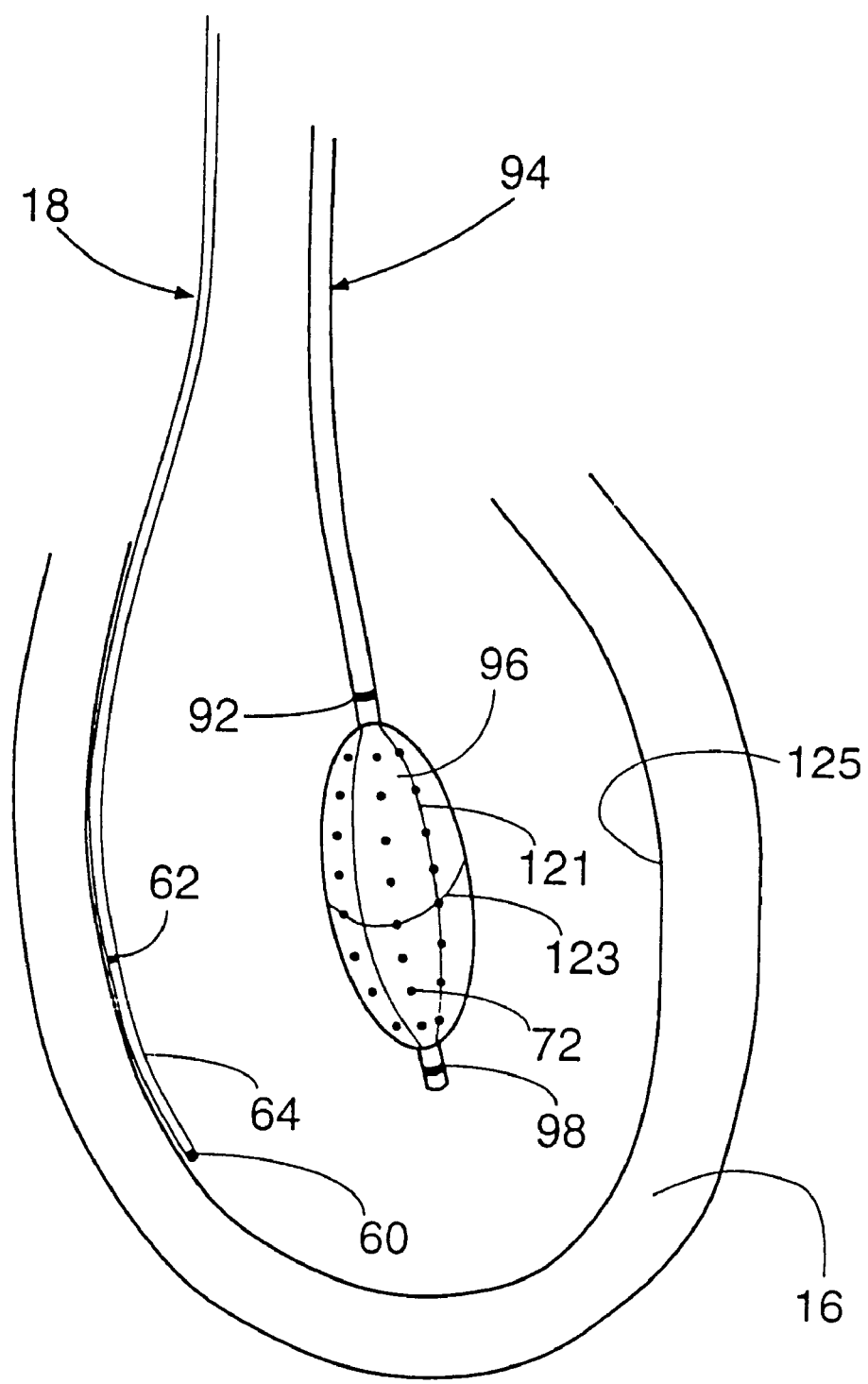
FIG. 3 is a diagram of an illustrative balloon electrode set implementation of the measurement catheter and a therapy catheter.

FIG. 3 shows an electrode configuration on a balloon catheter 94 which has an inflatable balloon 96 which underlies an array or set of passive electrodes 48 typified by passive electrode 72. These passive electrodes 48 can be organized into rows, typified by row 123, and columns, typified by column 121. A pair of active excitation electrodes 52 are typified by proximal electrode 92 and distal electrode 98. The balloon catheter 94 configuration can be quite small in comparison with the basket catheter 80 configuration. This small size is desirable both for insertion into and for use in a beating heart 16.

FIG. 3 also shows a movable, reference or therapy catheter system 18. This catheter is shown lying along the interior surface 125 of the heart 16. A pair of electrodes shown as delivery electrode 60 and reference electrode 62 are located a fixed distance apart on the catheter body 64. This auxiliary catheter may be used to supply ablation energy to the tissue during therapy. This therapy catheter 18 may be used with either the basket catheter 80 configuration or the balloon catheter 94 configuration.

Figure 4:
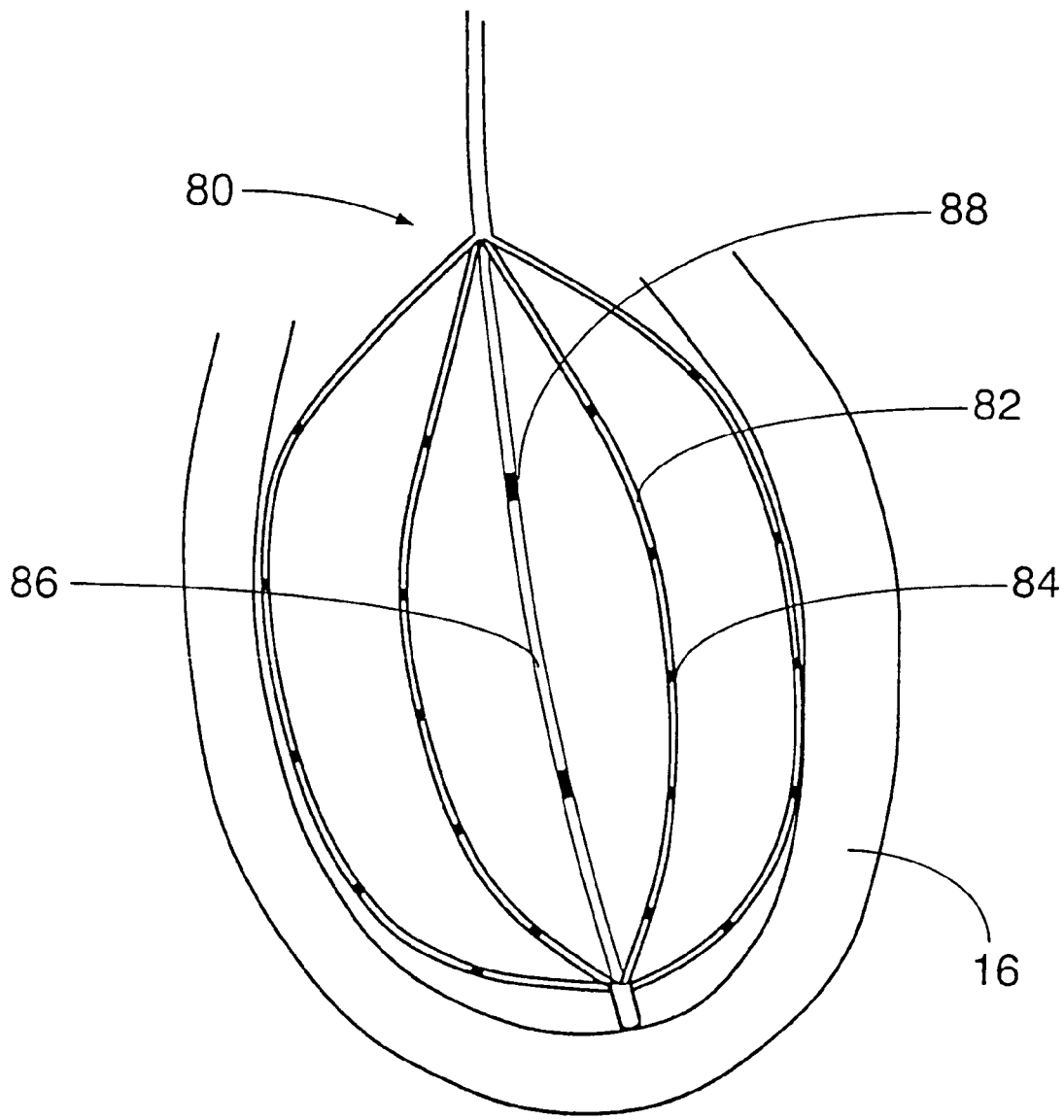
FIG. 4 is a schematic diagram of an illustrative basket electrode set implementation of the measurement catheter.

FIG. 4 shows an electrode configuration on a basket catheter 80. The limbs of the basket 80, typified by limb 82 carry multiple passive electrode sites typified by electrode 84. A pair of active excitation electrodes are shown on the central shaft 86 of the basket 80 as indicated by excitation electrode 88. The basket catheter 80 electrodes lie gently against the interior surface 125 of the heart 16 urged into position by the resilience of the limbs. The basket catheter 80 permits unimpeded flow of blood through the heart during the mapping procedure which is very desirable. This form of catheter also places the electrodes into contact with the heart chamber wall 125 for in-contact mapping of the physiologic potentials of the heart 16.

Returning to FIG. 1 and FIG. 2 these figures show one illustrative partitioning of system functions. In use, the signal generator 54 can generate a 4800 Hz sinusoidal signal burst on the active electrode set 52 which creates an electric field in the heart. The changing position of the chamber walls 125 and the, amount of blood within the heart determines the signal strength present at the passive electrode sites 48. For purposes of this disclosure the chamber geometry is derived from the electric field as measured at the passive electrode sites 48 which may, or may not be in contact with the walls 125 of the heart. In the case of the basket electrodes 84 which lie on the heart surface 125 the field strength is inversely proportional to the instantaneous physical wall location and the distance from the active electrodes 52 to these walls. In the case of the balloon catheter the potentials on the passive set of electrodes 72 are related to the wall location, but a set of computationally intensive field equations must be solved to ascertain the position of the wall. In general, both the basket and balloon approach can be used to generate the dynamic representation of the wall surface.

The computer 34 operates under the control of a stored program which implements several control functions and further displays data on a display device 36. The principal software processes are the wall surface generation process (WSGP); the body orientation generation process (BOGP); the wall electrogram generation process (WEGP); the site electrogram generation process (SEGP); and the movable electrode location process (MELP).

WALL SURFACE GENERATION PROCESS

Figure 5:
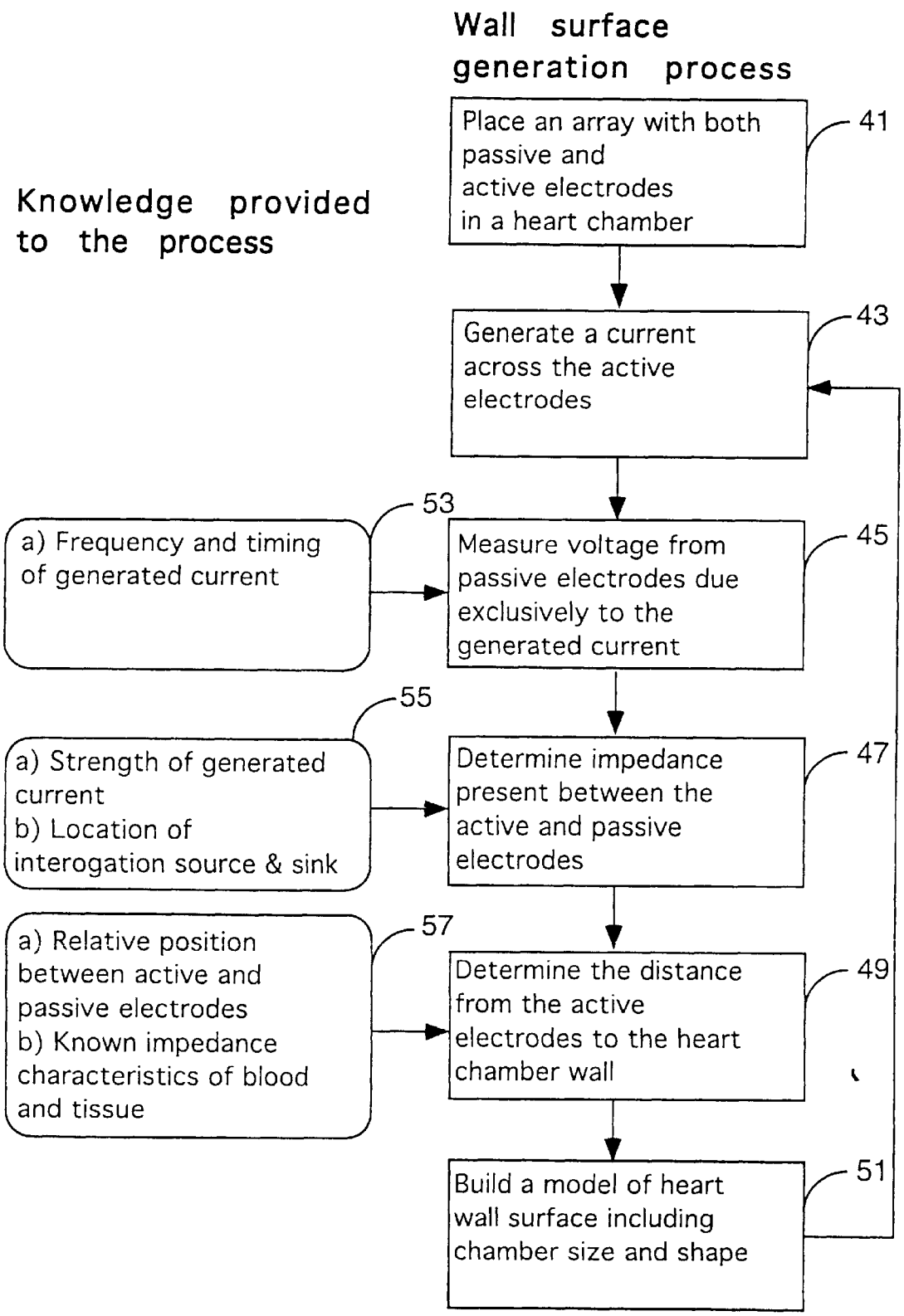
FIG. 5 is a flow chart showing the wall surface generation process.

FIG. 5 is a flow chart describing the method used to generate the "wall surface" of the interior of the heart 16. The step-wise processes are presented with certain physical parameters which are either known in advance by computation or are measured. This knowledge or information is shown in block 53, block 55 and block 57. The WSGP process begins at block 41 with the insertion of the monitoring catheter 14 in the heart 16. This catheter 14 places an array of electrodes 44 in a heart 16 chamber. This array must have both passive measurement electrode sites 48 and active interrogation electrode sites 52 located in a known position. The process enters a measurement and display loop at block 43 where an interrogation pulse burst is generated by the signal generator 54 seen in FIG. 2. These pulses are generated first with the current source at site 92 and the current sink at site 98 and second with the current source at site 98 and the sink at site 92 as seen in FIG. 3. At block 45 the signal conditioner 50 uses information on the frequency and timing of the interrogation current from block 53 to demodulate the signals and analog to digital convert the signals received at the passive measurement electrodes 48. At block 47 the information from block 55 is used. This information includes both the current strength of the interrogation pulse and the location of the interrogation source and sink electrodes. Impedance is voltage divided by current. The voltage offset caused by the location of the current source can be reduced by the two measurements of opposite polarity. This information is used to determine the impedance which the chamber and the blood contained in that chamber imposes on the field generated by the interrogation current. The knowledge from block 57 is used next. Block 49 determines how the heart chamber tissue, which has roughly three times the impedance of blood, in combination with the type of electrode array affects the field generated by the interrogation electrodes.

In a system as shown as the basket in FIG. 4 the blood effects the impedance directly as the field is propagated from the interrogation electrodes to the measurement electrodes. In general, if a point current course is used within a chamber the inverse of the measured voltage is proportional to the square root of the distance from the source. With the distance from each electrode 84 to both excitation electrodes 88 computed from the measured voltage and the known location of the electrodes 84 relative to each other, the locations of each electrode 84 can be determined.

In a system as shown in FIG. 3 the impedance of the field generated within the blood volume is modulated by the position of the walls 125, with their higher impedance, with respect to the location relative to the measurement electrodes. Using this knowledge and the measurements from block 47 the distance from the interrogation electrodes to the heart chamber wall 125 is determined at a point normal to the field generated by the active interrogation electrodes 52.

The passive electrodes 48 on the balloon catheter 94 can be positioned in rows 123 and columns 121 with the columns in a line from the top of the balloon 96 near active electrode 92 to the bottom of the balloon 96 near active electrode 98. In a preferred embodiment three configurations are possible: 8 rows and 8 columns, 7 rows and 9 columns, and 6 rows and 10 columns. In each such embodiment the measurements from any row 123 are treated independently. Using the 8 row, 8 column embodiment as an example, 8 measurements of distance are taken for any selected row of electrodes, giving a total of 64 measurements.

Figure 6:
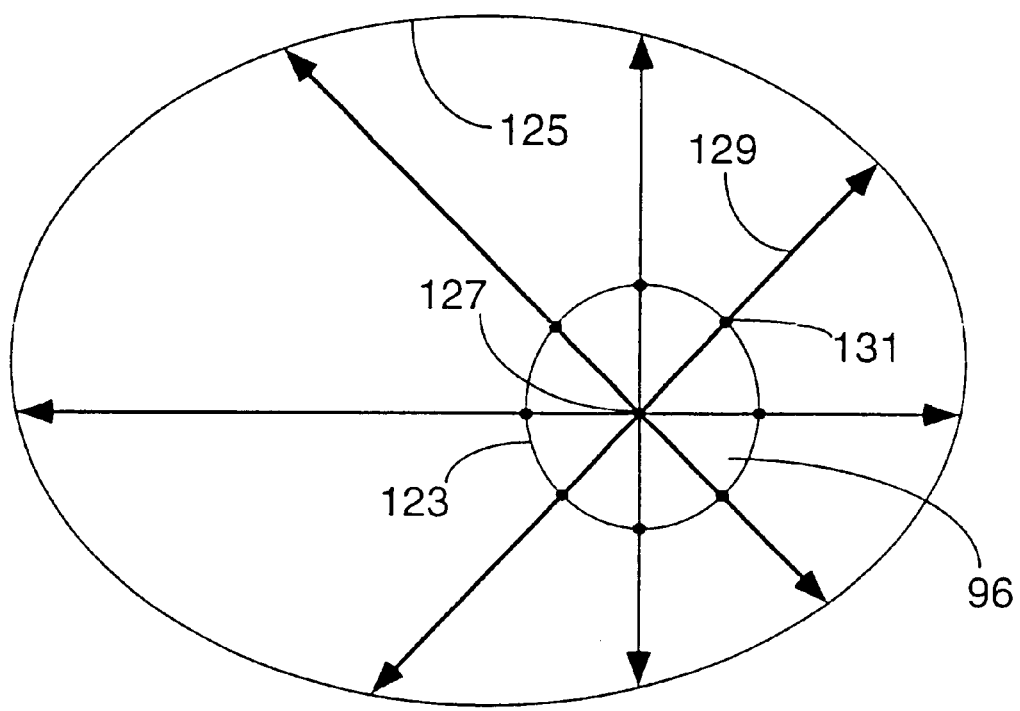
FIG. 6 is a schematic diagram of a row of electrodes of the balloon catheter and their use in measuring distance to the heart chamber wall.

FIG. 6 is a schematic drawing of the embodiment required to measure the distance 129 from the centroid 127 of the balloon 96 through the passive electrode 131 to the heart chamber wall 125. The passive electrode 131 is one of eight electrodes on a row of electrodes 123. Starting with electrode 131 and labeling it as electrode A, the other electrodes on the row 123 are labeled B, C, D, E, F, G and H by proceeding around the balloon 96 in a clockwise direction. The measurements of impedance "I" at these electrodes are thus labeled $I_A$, $I_B$, $I_C$, $I_D$, $I_E$, $I_F$, $I_G$ and $I_H$. To compute the distance 129 in the direction of electrode 131 the following equation is computed:

$$\ln(D_A) = c0 + c1*\ln(I_A) + c2*\ln(I_B) + c3*\ln(I_C) + c4*\ln(I_D) + c5*\ln(I_E) + c4*\ln(I_F) + c3*\ln(I_G) + c2*\ln(I_H)$$

where $D_A$ is the desired distance 129 and c0 through c5 are optimized parameters. A typical vector of these parameters is (c0, c1, c2, c3, c4, c5)=(3.26,−0.152,−0.124,−0.087,−0.078,−0.066).

Once the distance 129 in the direction of electrode 131 is determined then the computation can be redone by shifting this direction clockwise one electrode, relabeling electrodes A through H and solving the above equation again. Once the distances for this row of electrodes 123 are determined then the next row distances are determined in the same way until the distances at all 64 electrodes are determined.

Returning to FIG. 5, with multiple wall locations in space determined by this method, a model of the chamber wall 125 shape can be created in block 51. Various techniques for creating a shape are possible, including cubic spline fits, and best fit of an ellipsoid. The positions of the active electrodes 52 and the passive electrodes 48 relative to the heart 16 chamber walls are also determined at this point. The loop continues as the method moves back to block 43. This loop continues at a rate fast enough to visualize the real-time wall motion of the heart chamber, at least at twenty times per second.

There are numerous display formats or images which can be used to present the dynamic endocardial wall surface to the physician. It appears that one of the most useful is to unfold the endocardial surface and project it onto a plane. Wire grid shapes representing a perspective view of the interior of the heart chamber are useful as well. It appears that each individual physician will develop preferences with respect to preferred output image formats. In general, different views of the endocardial surface will be available or may be used for diagnosis of arrythmia and the delivery of therapy. One distinct advantage of the present invention is that the image of the heart wall is not static or artificial. In this system the image is a measured property of the heart wall, and is displayed in motion.

Figure 7:
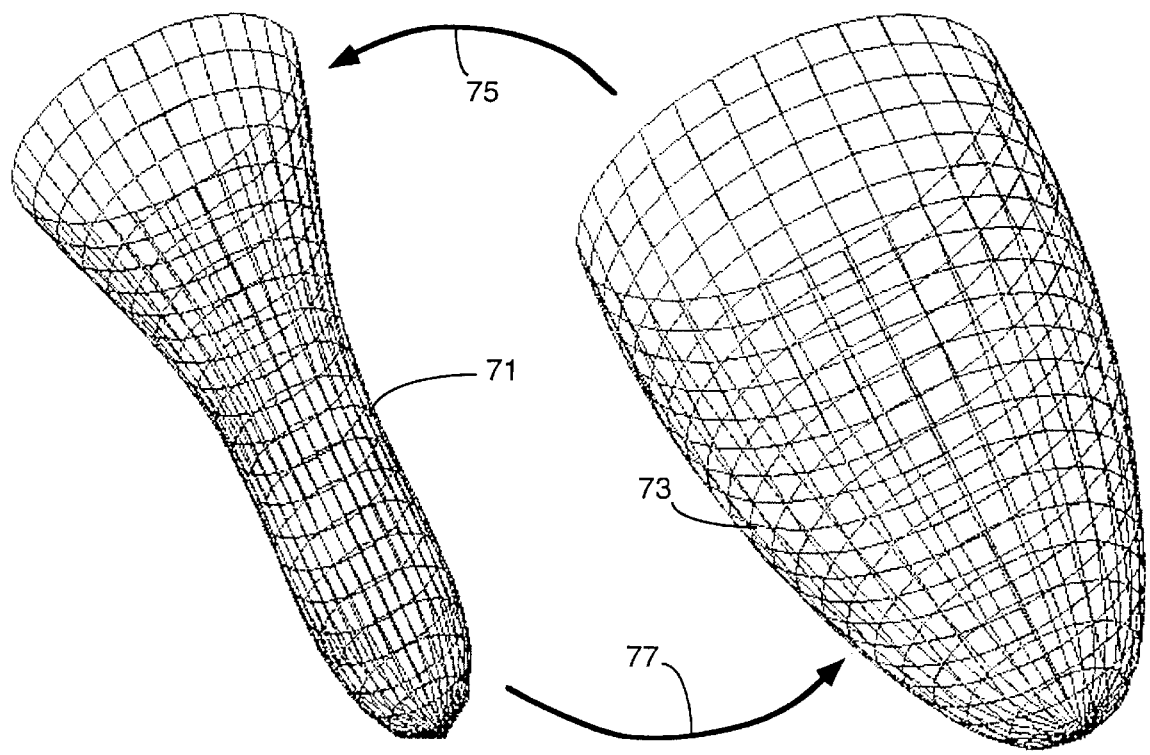
FIG. 7 is a screen display representing the motion of the cardiac wall surface.

FIG. 7 shows two separate frames of the dynamic representation of the heart wall. Wire frame 71 shows the heart at systole while wire frame 73 shows the heart at diastole. Path arrow 75 and path arrow 77 represent the dynamic cycling through several intermediate shapes between the systole and diastole representation. These views are useful as they indicate the mechanical pumping motion of the heart to the physician.

Body Orientation Generation Process

Figure 8:
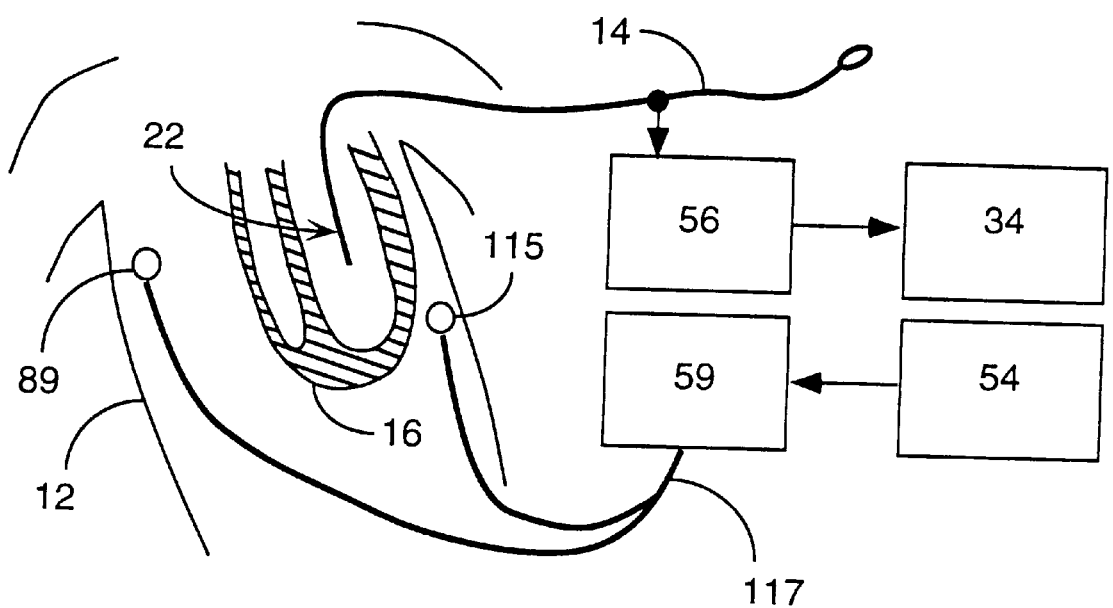
FIG. 8 is a schematic block diagram of the portion of the electrophysiology apparatus which implements the body orientation generation process.

FIG. 8 is a schematic drawing of the apparatus required to perform the body orientation generation process. It shows a patient 12 with at least one pair 119 of skin electrodes 40 attached to the body surface in a stationary position on the body and in a known configuration. These electrodes are typified by example surface electrodes 89 and 115 each of which could be an ECG electrode 74, an RF generation current sink electrode 70, or another electrode specifically dedicated to the BOGP. Ideally, electrode 89 and 115 are opposite one another on the body with the heart 16 directly in between them. This pair of electrodes is attached to the signal generator 54 through the switch 59 via an appropriate cable 117. The distal end 22 of monitoring catheter 14 is situated in the heart 16 where the passive electrodes 48 can measure the signals generated across the electrode 89 and electrode 115.

Figure 9:
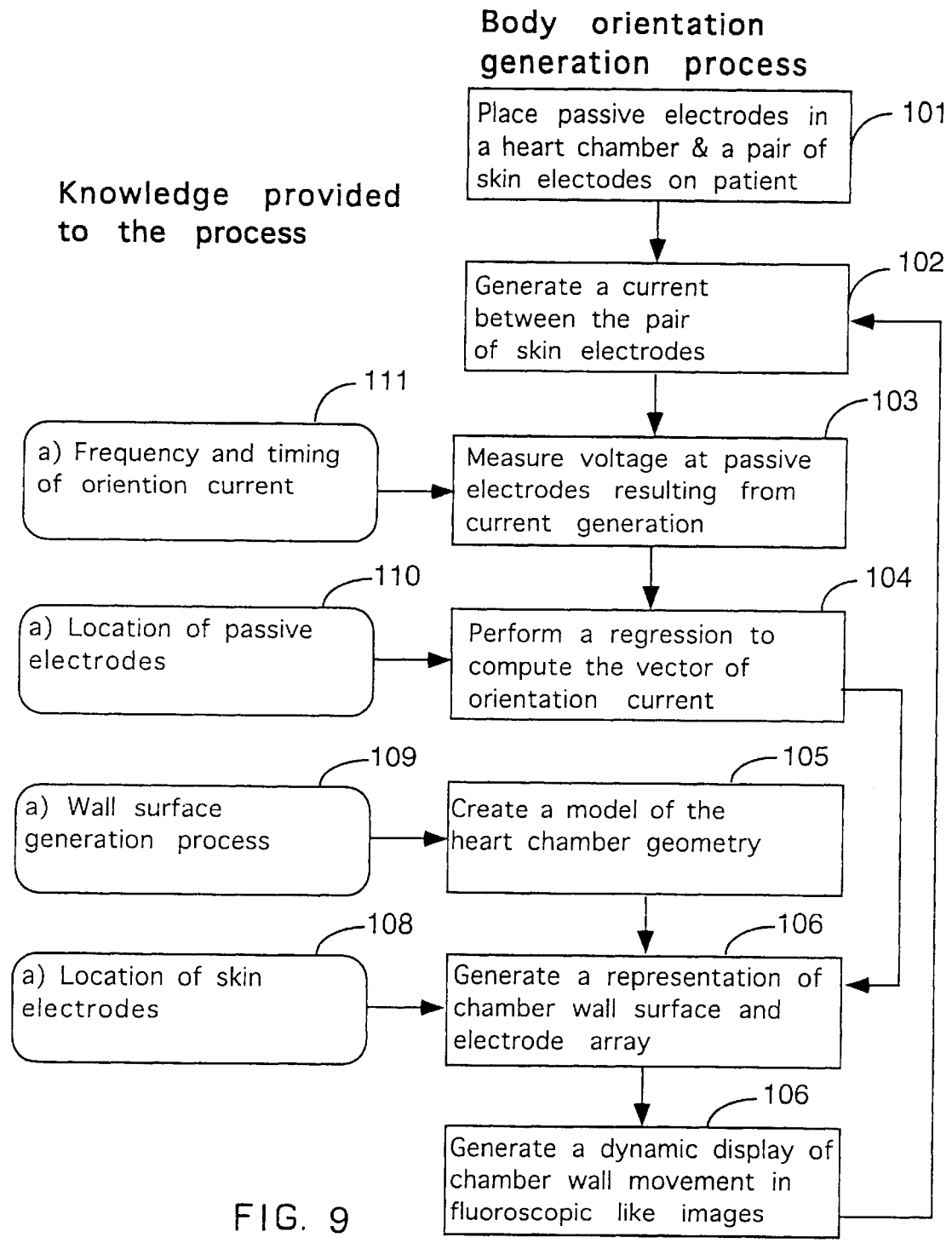
FIG. 9 is a flow charting showing the body orientation generation process.

FIG. 9 is a flow chart describing the method used to align the wall surface representation of the WSGP to the body orientation. The process begins at step 101 where the monitoring catheter 14 with a set of passive electrodes 48 is inserted into heart 16 chamber and a pair of surface electrodes 119 are attached at a known position on the body 12. The process begins cycling at step 102 where the signal generator 54 generates a signal across the skin electrode 89 and skin electrode 115. At step 103 the voltage created by the signal generator 54 is measured from passive electrode 48 by the high pass section 56 of the signal conditioner 50 by using the information from block 110 which includes the frequency and timing of the field generated by the signal generator 54. This voltage information is stored in an array "Y".

At step 104 a regression analysis is performed which creates a vector which lines up with the field generated in step 103. This regression method is the same whether a basket catheter as shown in FIG. 4 or a balloon catheter as shown in FIG. 3 is used. The location of each passive electrode 48 is provided to the method by block 110. This information comes from different sources in each case however. In the case of a basket catheter 80 these three dimensional electrode locations come from the WSGP. In the case of the balloon catheter 94 these three dimensional electrode locations are known a priori. In each case they are saved in an array "X". The regression to compute the orientation vector uses the standard regression equation for the computation of a slope:

$$b = \Sigma xy / \Sigma x^2$$

where "X" is the array of electrode locations, "Y" is the array of measured voltages and "b" is the orientation vector. If more than one pair of skin electrodes are used then an orthogonal set of orientation vectors can be created and any rotation of the monitoring catheter 14 relative to the body 12 can be detected.

In step 105 the information on the location of the chamber walls 125 from the WSGP 109 can be used to create a three dimensional model of the heart 16 chamber as seen in FIG. 7. By combining this model with the computed orientation from step 104 and the known location of the skin electrodes 108 this representation can be shown in a known orientation relative to the body in step 106. In step 107 a specific orientation such as typical radiological orientations RAO (right anterior oblique), LAO (left anterior oblique), or AP (anterior/posterior) can be presented. By repeatedly showing this view a dynamic representation can be presented which matches the view shown on a standard fluoroscopic display. Thus such an image can be presented without the need for using ionizing radiation.

Wall Electrogram Generation Process

Figure 10:
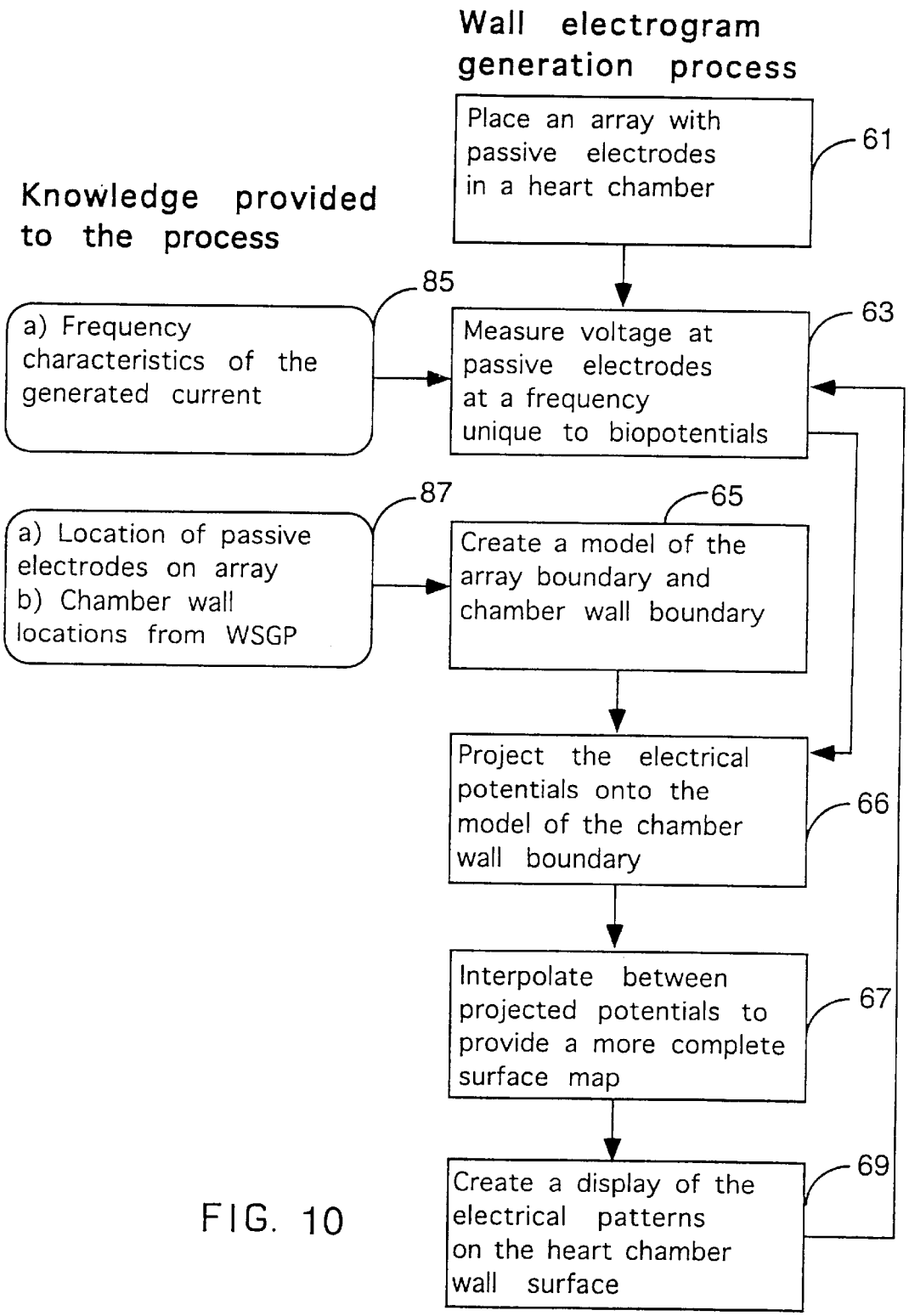
FIG. 10 is a flow chart showing the wall electrogram generation process.

FIG. 10 is a flow chart describing the wall electrogram generation process (WEGP). This process begins at block 61 when a monitoring catheter 14 with an array of passive measurement electrodes 48 is placed in a heart chamber 16 and deployed. The process enters a loop at block 63. The frequency of the interrogation pulses generated by the signal generator 54 is provided by block 85. With this knowledge the low pass filter section 58 of the signal conditioner 50 measures the voltage at frequencies lower than the generated interrogation pulses. Typically the highest frequency of the biopotentials is 100 Hz but can be as high as 250 Hz.

In the case of a basket system as seen in FIG. 4 the measurements are contact voltages from the chamber wall 125 tissue contacting the electrodes 84.

In the case of a balloon system as seen in FIG. 3 the measurements are measurements of the field generated throughout the blood volume by the tissue on the chamber wall 125. At step 65, a model of the array boundary and the chamber wall 125 boundary is created from the information in block 87. This information includes the location of the passive electrodes 48 on the array and the chamber wall 125 locations from the WSGP.

In the case of a basket system as seen in FIG. 4, the array boundary and the chamber wall 125 boundary are the same since they are in contact. The locations are determined in three-dimensional space of the sites on the chamber wall where potentials are measured.

In the case of the balloon system as seen in FIG. 3, the array boundary and the chamber wall 125 boundary are different. During step 65, locations are generated in three-dimensional space of the sites on the chamber wall where potentials are to be determined.

At step 66, the potentials are projected on to the sites on the chamber wall specified in step 65. In the case of a basket system as seen in FIG. 4, the measured potentials are assigned to these sites.

In case of a balloon system as seen in FIG. 3, a three dimensional technique such as those typically used in field theory is used to generate a representation of the three dimensional field gradients in the blood volume of the heart chamber. Two examples of appropriate techniques are a spherical harmonics solution to Laplace's equation, and boundary element analysis. A more detailed description of spherical harmonics is given in the parent disclosure which is incorporated by reference herein.

For the boundary element method in the mapping system of the invention, the voltage is measured at the passive electrodes 48 on the probe or balloon catheter 94. From the voltage at the electrodes on the probe and the knowledge that the probe is nonconducting, the voltage and normal current at a previously selected set of nodes on the endocardial surface 125 are determined by the boundary element method in the following manner.

It is known that the voltage in the blood pool between the probe and the endocardium satisfies Laplace's equation that states that the net current flow across any specific boundary is zero. To find the voltage and/or normal current on the endocardium, one must find the solution of Laplace's equation in the blood pool and calculate the values of this solution on the endocardium. Standard finite element and finite difference methods can be used to find the solution to Laplace's equation, but they have large computational overhead for generating and keeping track of a three-dimensional grid in the whole blood pool. In the mapping system of the invention, Laplace's equation is solved by the boundary element method, a specialized finite element method that permits one to restrict the calculations to the two-dimensional probe and endocardial surfaces (and not have to deal with calculations over the blood pool between these two surfaces). In order to create an accurate map of the endocardial voltage and/or normal current based on the voltage information from a limited number of electrodes on the probe, the system uses a higher-order version of the boundary element method. This system currently uses bicubic splines to represent the probe and endocardial surfaces and bilinear elements and bicubic splines to represent the voltage and the normal current on these surfaces.

The boundary element method consists of creating and solving a set of linear equations for the voltage and the normal current on the endocardium based on the voltage measurements at the electrodes on the probe. Each of the elements in the matrices that are involved in this set consists of two-dimensional integrals, which are calculated by numerical and analytical integration.

Using Laplace's equation with data given on the probe is a so-called "ill-posed" problem. For such problems, all solution procedures, including the boundary element method, are ill conditioned, that is, small errors in the measured voltage on the probe surface can result in large errors in the calculated voltage and/or normal current on the endocardium. To minimize the errors on the endocardium, options for regularization or constraints have been included in the software code. For example: the user can choose parameters that cause the code to add equations for known or expected values of the voltage and/or normal current on the endocardium. This capability is often but not exclusively used to add equations that take into account the voltage and/or normal current of the map of the previous instant(s) in time (the previous "frame(s)"). This process uses historical data from the previous frame to constrain the values subsequently computed.

The solution of the set of the boundary element equations and regularizing equations (if any) is normally accomplished by singular value decomposition but there is an option to solve the linear system by decomposition (Gaussian elimination) or direct or inherent methods. When singular value decomposition is used, there is an option to turn off the influence of high-frequency errors (that is, do a type of regularization) by setting various small singular values to zero, the result of which can be an increase in the accuracy of the calculated voltage and normal current on the endocardium.

In block 67, a large number of points are calculated on the three-dimensional chamber surface 125. In the case of a basket catheter as seen in FIG. 4, this is done through interpolation using bilinear or bicubic splines. In the case of a balloon catheter as seen in FIG. 3, this can be done either by using the model, such as the boundary element method or spherical harmonics to generate more points. Alternatively, bilinear or bicubic splines can be used to interpolate between a smaller number of points.

Figure 11:
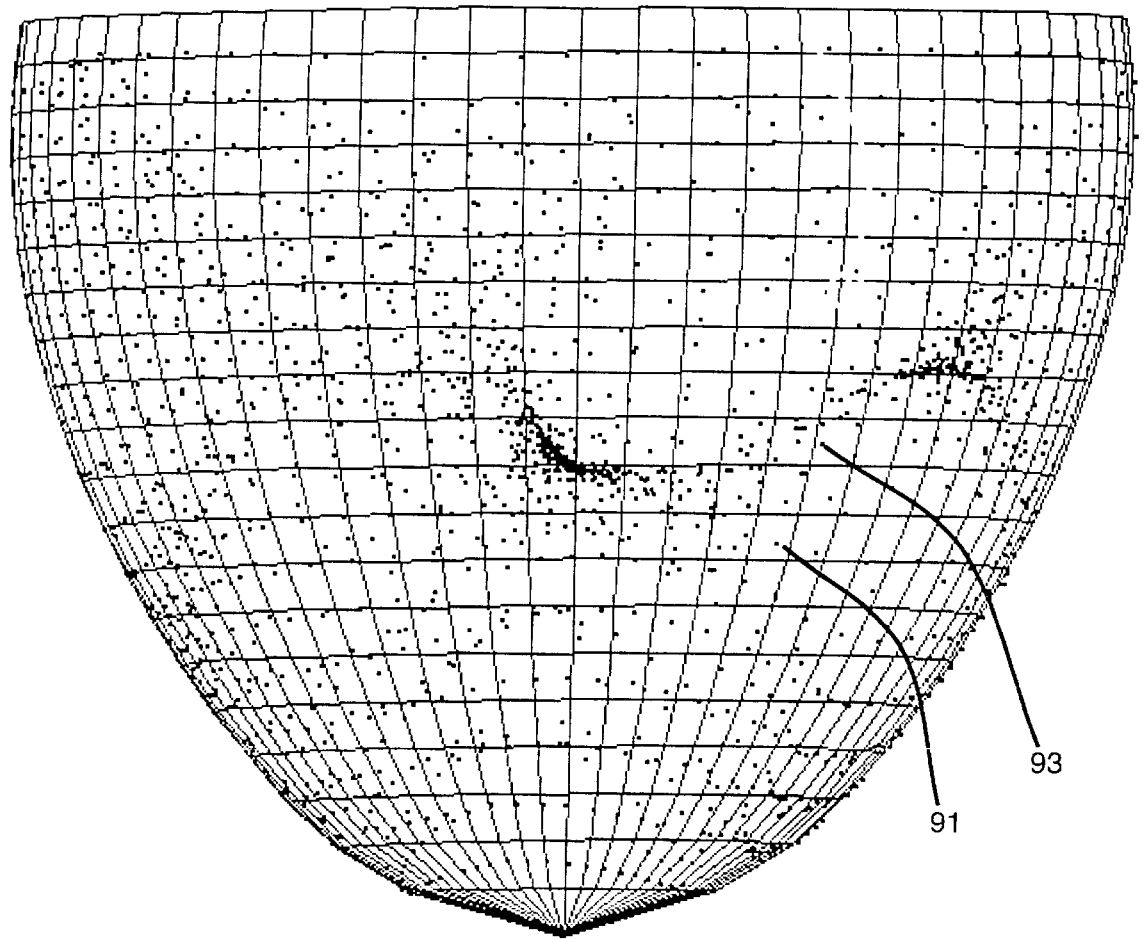
FIG. 11 is a representative screen display showing wall electrogram information.
Figure 12:
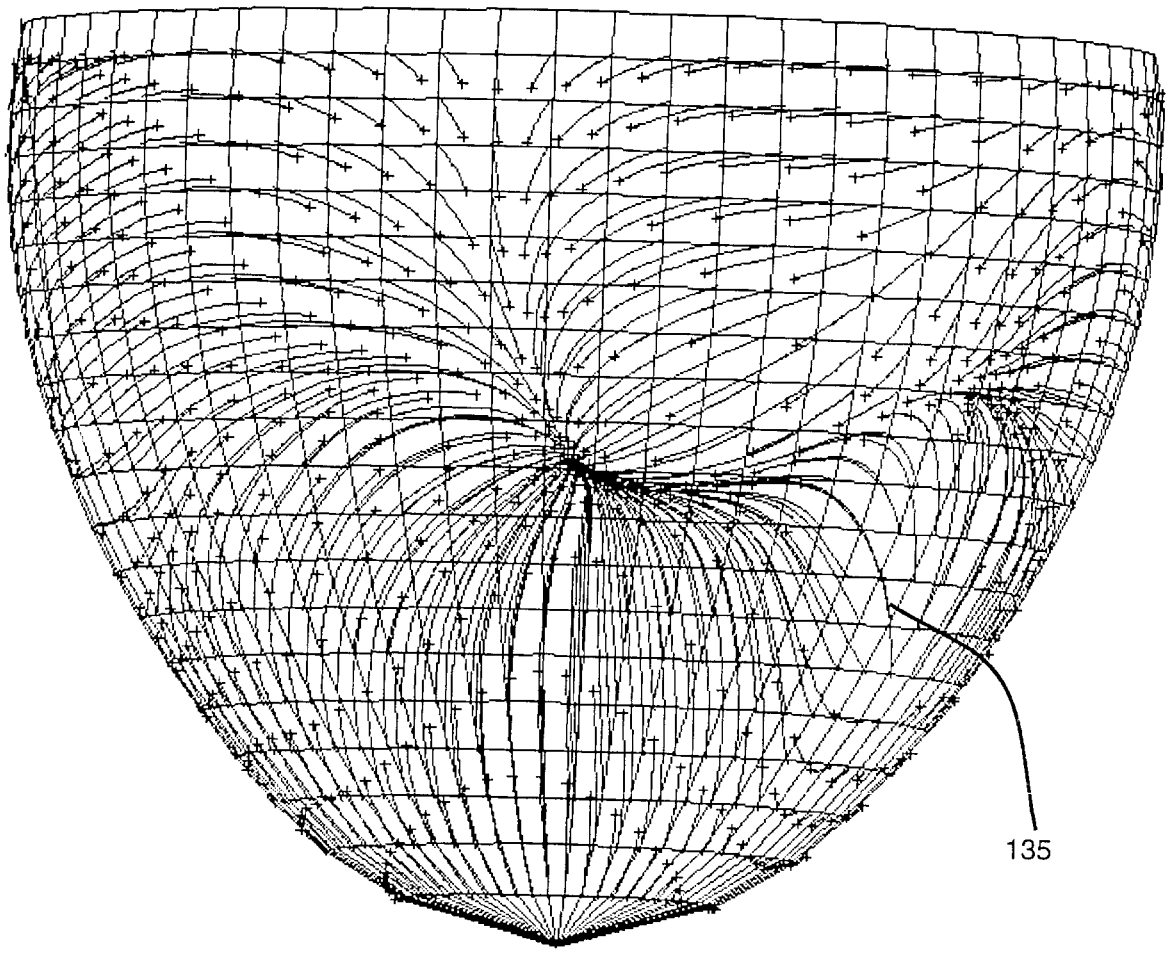
FIG. 12 is a representative screen display showing wall electrogram information.
Figure 13:
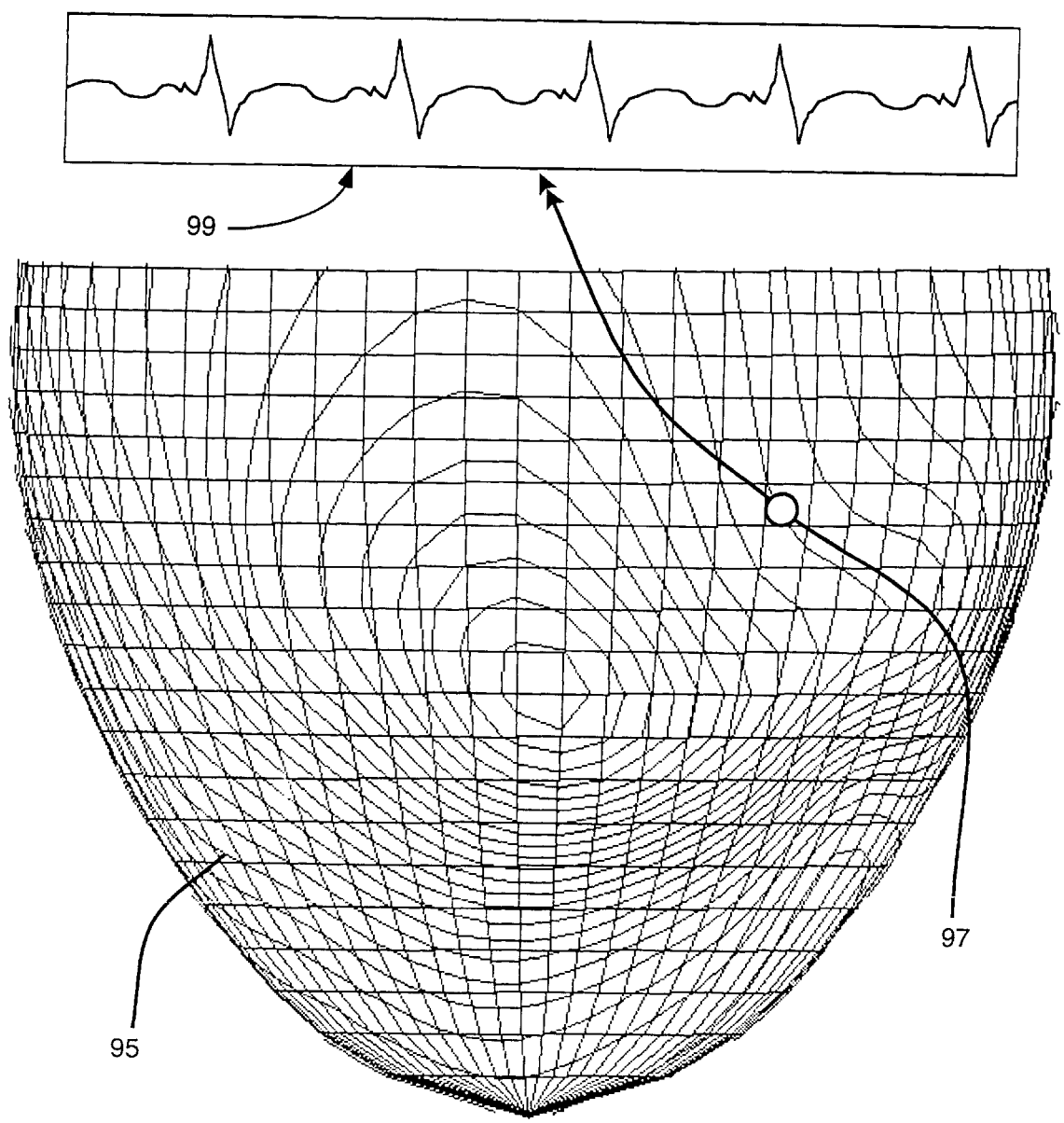
FIG. 13 is a representative screen display showing wall electrogram information.

In block 69 a representation of the electrical potentials on the surface 125 are used to display the patterns. These types of displays include color maps, maps of iso-potential lines, maps of potential gradient lines and others. The electrophysiologic information is reconstructed on the dynamic wall surface 125. In general the measured electrical activity is positioned by the WSGP at the exact location which gives rise to the activity. The high resolution of the system creates an enormous amount of information to display. Several techniques may be used to display this information to the physician. For example the electrogram data can be shown in false color gray-scale on a two dimensional wall surface representation. In this instance areas of equal potential areas are shown in the same color. Also a vectorized display of data can be shown on a wire grid as shown in FIG. 11 where the distance between any two dots typified by dot pair 91 and 93 represent a fixed potential difference. The more active electrical areas show clusters of dots. In a dynamic display the dot movement highlights areas of greater electrical activity. In FIG. 12 gradient lines typified by line 135 represent the change in potential over the chamber wall surface. Those areas with the largest change per unit area have the longest gradient lines oriented in the direction of steepest change. In FIG. 13 iso-potential lines typified by line 95 represent equal electrical potential. In this representation the closeness of lines represents more active electrical areas.

Site Electrogram Generation Process

Figure 14:
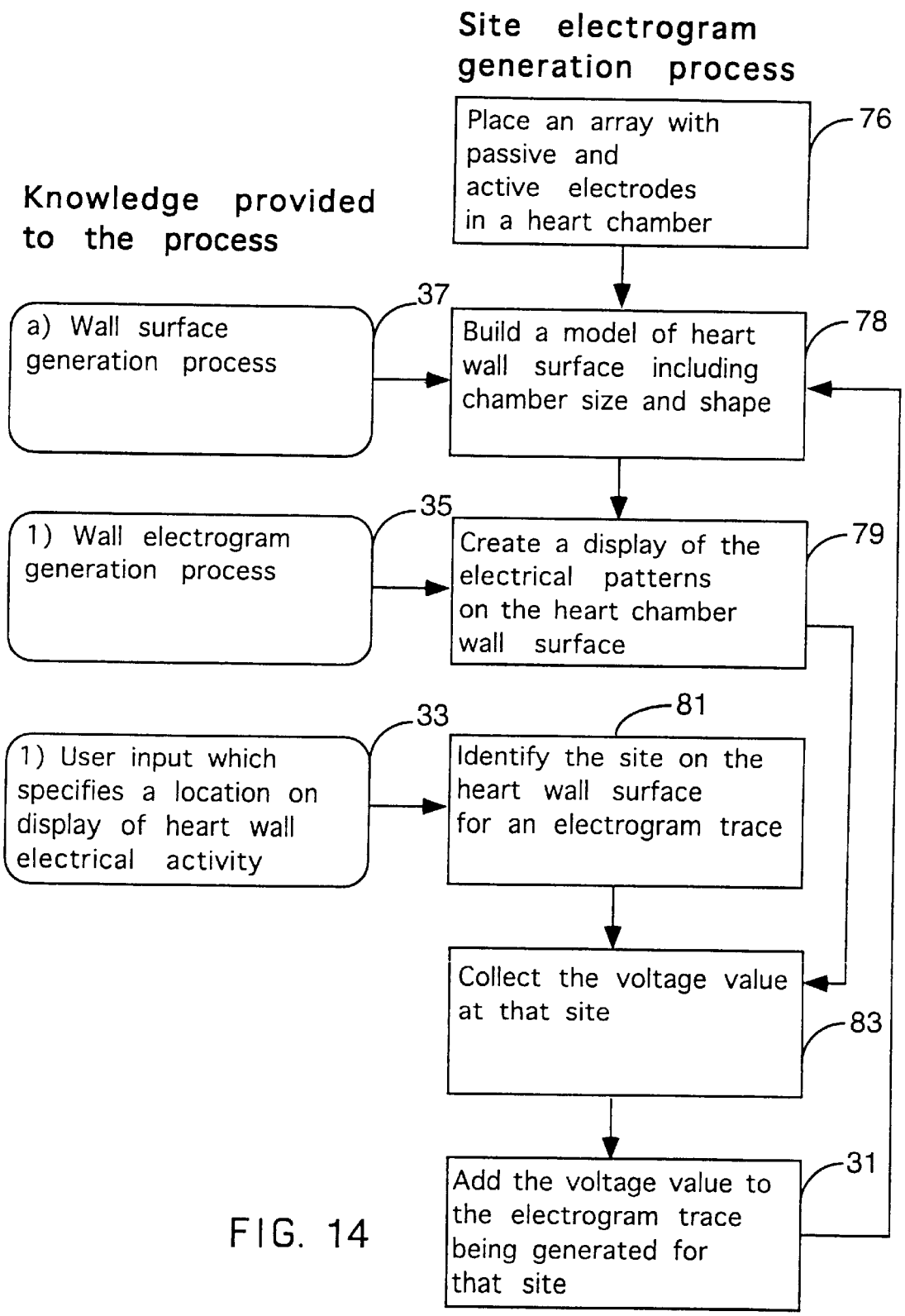
FIG. 14 is a flow chart showing the site electrogram generation process.

FIG. 14 is a flow chart of the site electrogram generation process (SEGP). This process is used to extract and display a time series representation of the electrical activity at a physician selected site. FIG. 13 shows a site 97 that has been selected and a time series electrogram 99 is shown on the display device 36 along with the dynamic wall representation. Returning to FIG. 14 this process begins at block 76 when a catheter with an array with both passive measurement electrodes 48 and active electrodes 52 is placed in a heart chamber and deployed. The process enters a loop at 78. The inputs to the method include the wall locations from block 37. Then the wall electrogram generator 35 provides the electrical potentials on this surface at 79. The user will use the display 36 to determine a location of interest in block 33 which will then be marked on the display device 36 at step 81. The voltage from this location will be collected at block 83. This voltage will be plotted in a wave-form representation 99 in block 31. The loop continues at this point at a rate sufficient to display all of the frequencies of such a time series electrogram 99, at least 300 points per second.

The false color and vectorized display images may direct the physician to specific sites on the endocardial surface for further exploration. The system may allow the physician to "zoom" in on an area to show the electrical activity in greater detail. Also the physician may select a site on the endocardial wall 125 and display a traditional time series electrogram 99 originating at that site.

Movable Electrode Location Process

Figure 15:
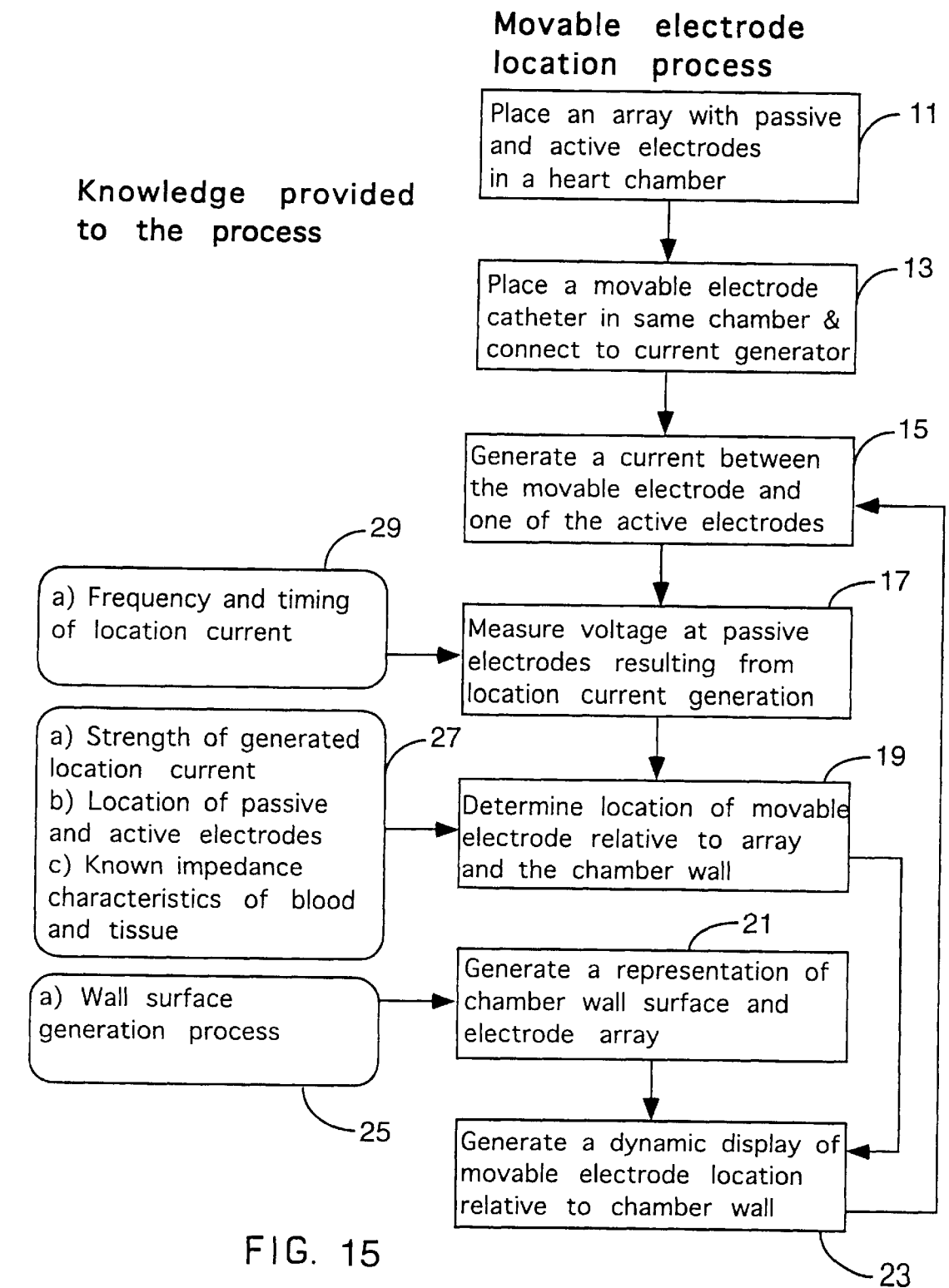
FIG. 15 is a flow chart showing the movable electrode location process.

FIG. 15 is a flow-chart of the movable electrode location process (MELP). It begins at block 11 when a catheter with an array of passive measurement electrodes 48 and active electrodes 52 is placed in a heart 16 chamber and deployed. At block 13 a second catheter 18 with at least one electrode is introduced into the same chamber. The process enters a loop at block 15 where the signal generator 54 generates a carrier current between the movable location electrode 68 and an active electrode 52. At block 17 the high pass section 56 of signal conditioner 50, using the frequency and timing information of the location signal from block 29, produces measured voltages from the passive measurement electrodes 48. At block 19 the information from block 27 is used to determine the location of the electrode 68 where the location current is generated. This information includes the strength of the generated location current, the impedances of blood and tissue, the location of the active electrode 52 in use and the location of all the passive measurement electrodes 48. One method for using this information would entail performing a three dimensional triangulation of the point source location signal using four orthogonal passive electrode 48 sites. The implementation of step 19 is the same both for the case of a basket system as seen in FIG. 3 and for the case of a balloon system as seen in FIG. 4. In this preferred implementation, two data sets are acquired closely spaced in time such that they are effectively instantaneous relative to the speed of cardiac mechanical activity. Alternatively, the data sets could be acquired simultaneously, by driving signals at two different frequencies, and separating them electronically by well known filtering means.

The first data set is acquired by driving the current carrier from the location electrode 68 to a first sink or active electrode as typified by electrode 98. This electrode is at a known location on the body of the monitoring catheter 14 relative to the array of passive electrodes 48. The location of this first sink electrode is ideally displaced distally from the centroid 127 of the array of electrodes by at least 25 millimeters. A second data set is then acquired by driving the current from the location electrode 68 to a second active electrode 92, located ideally at least 25 millimeters proximally from the centroid 127 of the array of electrodes.

The location algorithm is performed by minimizing the following equation:

$$\sum_{i=1}^{n}\left(\frac{k}{\left(\vec{R}_i - \vec{R}_L\right)^{0.5}} - V_{pi_1} - b_1 - \frac{k}{\left(\vec{R}_i - \vec{R}_{S_1}\right)^{0.5}}\right)^2 +$$

$$\left(\frac{k}{\left(\vec{R}_i - \vec{R}_L\right)^{0.5}} - V_{pi_2} - b_2 - \frac{k}{\left(\vec{R}_i - \vec{R}_{S_2}\right)^{0.5}}\right)^2$$

Where n is the number of array electrodes, where k, $b_1$ and $b_2$ are fitting parameters, $V_{pi}$ are the potentials measured from each $i^{th}$ electrode 72, $R_i$ is a vector from the origin (centroid of the array of electrodes 96) to the $i^{th}$ probe electrode 72, $R_L$ is the "location vector", or three dimensional location to be solved for in the minimization, and $R_{s1}$, $R_{s2}$ are the location vectors of the active sink electrodes (eg. 92 and 98) which are known at locations on the axis of the array of passive electrodes 48.

Additional data sets could be incorporated, following the same logic as above. Each additional squared parenthetical term requires the probe data set Vpi, another 'b' fitting term, and the particular active sink electrode 52 vector $R_s$ used during the acquisition of that data set. If the sink electrode 52 is far enough away, for example using a right leg patch electrode, the fourth term in the squared expression for that data set may be deleted as $R_s$ becomes very large.

It is also noted that the method does not require two data sets. The first squared expression in the above expression (requiring only data set $V_{pi1}$) may be sufficiently accurate.

The non-linear least squares minimization may be performed on the above summation by any of several well-known methods. The Levenberg-Marquardt method has been used in practice to accomplish this with efficient and robust results. Nominal values for k and b are 70 and 0 respectively, when normalizing the potential values obtained as if the current source were 1 ampere. The number of parameters in the minimization for the above expression are six: k, $b_1$, $b_2$, and the x, y, and z coordinates of vector $R_L$ (assuming a Cartesian coordinate system with origin at the center of the array of electrodes 96).

At step 21 a model of the heart 16 chamber wall is generated from the information provided from the WSGP 25. Such a model can be represented on a display 36 in a manner typified in FIG. 6. Once this surface is rendered, within this surface a second figure representing the distal end of the monitoring catheter 14 can be presented. In this way, the full three dimensional geometry of the chamber and the array catheter can be presented.

In step 23 this geometry is updated repeatedly to provide a dynamic view of the chamber, the monitoring catheter 18, along with a representation of the distal end 24 of the therapy catheter 18. If this is then combined with the electrical potentials generated by the WEGP, the therapy catheter can be moved to an electrical site of interest represented by a point in three dimensional space.

Calibration Process

Calibration of the system to insure that physical dimensions are accurately scaled is not a necessity for use of the system in a diagnostic or therapeutic setting. However, the availability of heart geometry in real time can permit various hemodynamic measurements to be made and displayed to the physician as well. These measurements include systolic time intervals, stroke volume and cardiac output. Calibration, where desired, requires at least two electrodes 60 and 62 a known distance apart placed along the innersurface of the heart chamber 16, as shown in FIG. 3. In general the two electrode sites will each be coupled to the location signal generator 54. The MELP of FIG. 15 can be calibrated by scaling the calculations 50 the distance between computed locations match the known distance apart of the two electrodes 60 and 62. Since the electrodes 60 and 62 are positioned on the chamber wall 125, the WSGP of FIG. 5 can be calibrated by scaling the distance measured by the WSGP in the direction of electrodes 60 and 62 to the calibrated distances measured by MELP. Finally, since the electrodes are contacting the chamber wall and providing electrograms, the WEGP of FIG. 10 and SEGP of FIG. 14 can be calibrated to those measurements by computing the voltages at the same locations on the chamber wall 125 where electrodes 60 and. 62 are located. These computed voltages can then be scaled to match the physically measured voltages from electrodes 60 and 62.

Therapy Catheter

Figure 16:
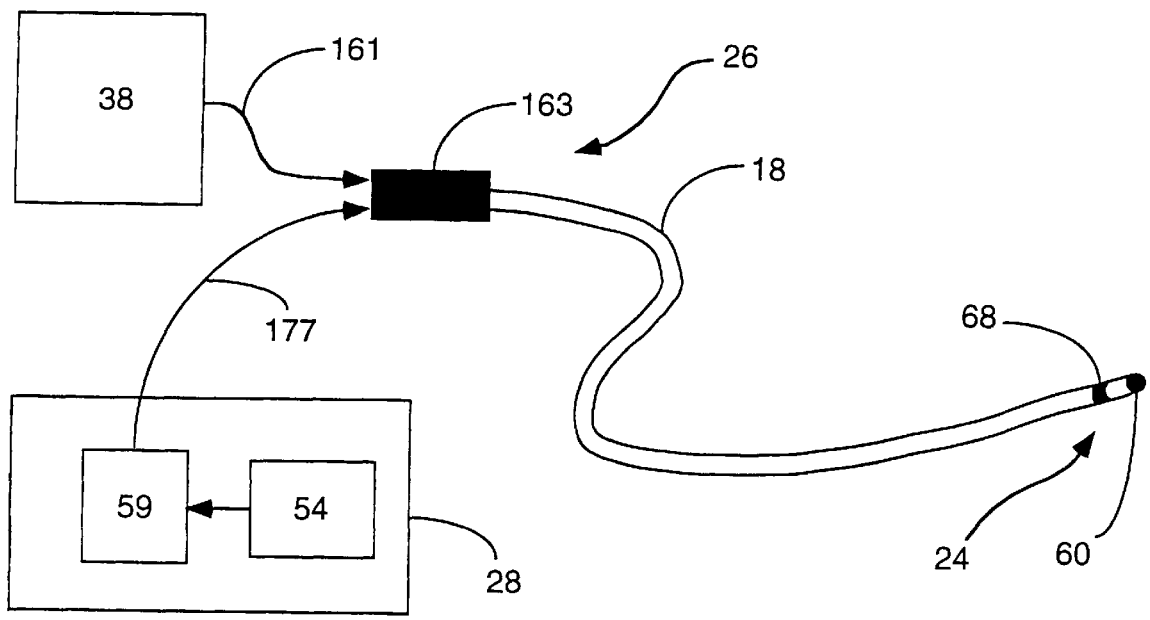
FIG. 16 is a schematic block diagram of the therapy catheter system.

FIG. 16 is a schematic diagram of the therapy catheter system. The therapy catheter 18 has both a distal end 24 and a proximal end 26. A handle 163 is on the proximal end 26 which allows the user to manipulate the distal end 24 and position it in the heart 16. Referring to FIG. 1, this handle also permits the therapy catheter 18 to connect to the interface system 28 of the electrophysiologic apparatus 10 through the cable 32. The location current is generated by the signal generator 54 through the switch 59 and subsequently through the wire 177 of cable 32 which is connected directly to the locator electrode 68. The therapy catheter system also includes a therapy generator 38 which is connected to the therapy catheter handle 163 via therapy supply line 161. The therapy supply line 161 extends through the handle 163, through the catheter body 64, to the therapy deployment apparatus 60 at the distal end 24 of the catheter. The locator electrode 68 is in close proximity to the therapy deployment apparatus 60 in order to determine its location within the heart 16.

Figure 17:
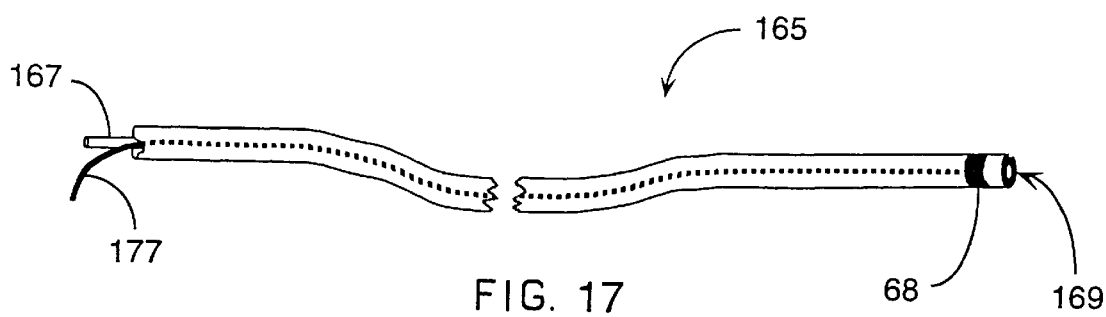
FIG. 17 is a schematic diagram of the laser delivery embodiment of the therapy catheter.

FIG. 17 shows an embodiment of the therapy catheter 18 using laser energy to supply the therapy. This laser catheter 165 includes the location wire 177 which connects the interface system 28 to the locator electrode 68 at the catheter's distal end 24. In this instance the therapy supply line 161 is a fiber optic cable 167 and the therapy deployment apparatus 60 is a fiber optic terminator 169 which directs the laser energy to the site of therapy delivery.

Figure 18:
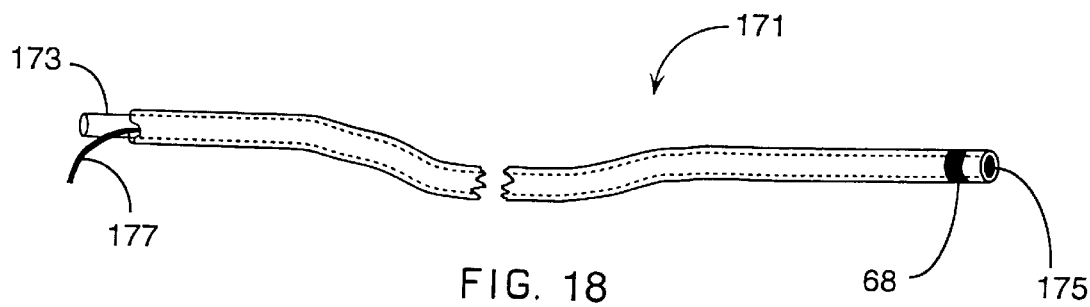
FIG. 18 is a schematic diagram of a microwave delivery embodiment of the therapy catheter.

FIG. 18 shows an embodiment of the therapy catheter 18 using microwave energy to supply the therapy. This microwave catheter 171 includes the location wire 177 which connects the interface system 28 to the locator electrode 68 at the catheter's distal end 24. In this instance the therapy supply line 161 is a microwave wave guide 173 and the therapy deployment apparatus 60 is a microwave emitter 175 which directs the microwave energy to the site of therapy delivery.

Figure 19:
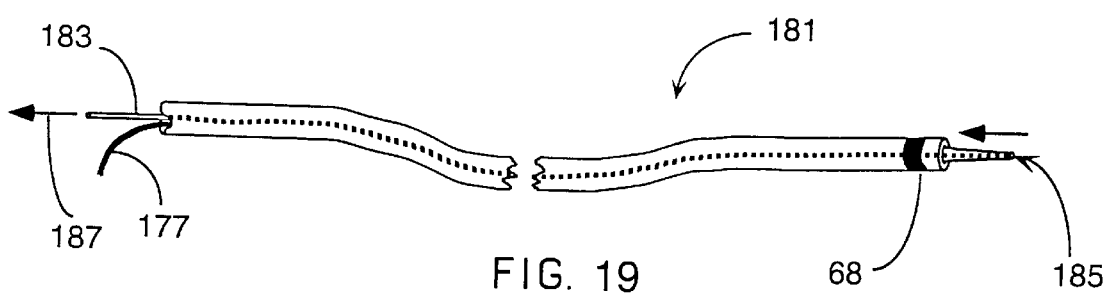
FIG. 19 is a schematic diagram of a chemical delivery embodiment of the therapy catheter.

FIG. 19 shows an embodiment of the therapy catheter 18 using a chemical to supply the therapy. This chemical deliver catheter 181 includes the location wire 177 which connects the interface system 28 to the locator electrode 68 at the catheter's distal end 24. In this instance the therapy supply line 161 is a chemical filled lumen 183. This lumen extends to the distal end 24 of the chemical delivery catheter 181 where a needle 185 is used to infuse the chemical into the heart chamber wall 125. During introduction of the chemical delivery catheter 181 into the heart chamber the needle 185 is withdrawn into the catheter body through withdrawal action 187. Once the location of the distal end 24 is determined to be at the site of interest the chemical delivery needle 185 can be deployed through the reverse of withdrawal action 187. Potential chemicals to be used in the therapeutic delivery process include formaldehyde and alcohol.

Each of the therapy catheters 18 shown in FIG. 17 through FIG. 19 as well as the radio frequency catheter shown in FIG. 2 can be miniaturized and inserted into the coronary arterial tree. The location signal generated at locator electrode 68 can still be sensed by the passive electrodes 48 even though the signal is coming from the epicardium of the heart 16 rather than from within the heart chamber. Thus the movable electrode location process of FIG. 15 can be used in this instance to help determine the location of the distal end 24 of the therapy catheter 18 in the coronary arterial tree and whether it is close to a site of abnormal electrical activity. Assuming that a site of ischemia will commonly be a site of abnormal electrical activity, the MELP will also enable more rapid location of potential sites for angioplasty.

Figure 20:
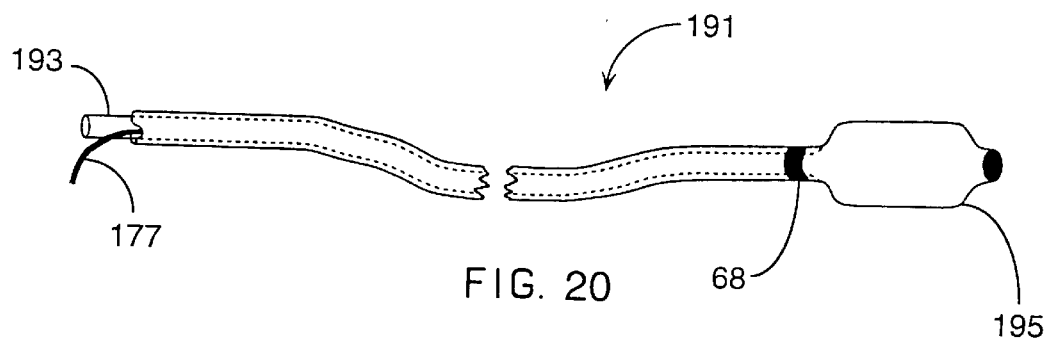
FIG. 20 is a schematic diagram of the angioplasty catheter embodiment of the therapy catheter.

FIG. 20 shows an embodiment of the therapy catheter 18 using balloon inflation to supply the therapy. This angioplasty catheter 191 includes the location wire 177 which connects the interface system 28 to the locator electrode 68 at the catheter's distal end 24. In this instance the therapy supply line 161 is an inflation media supply lumen 193 and the therapy deployment apparatus 60 is an angioplasty balloon 195. In use, a site of interest would be determined after viewing the wall electrogram generated by the WEGP of FIG. 10. Next the angioplasty therapy catheter 191 would be positioned in the coronary arterial tree and its position determined relative to the site of interest. Next, when the distal end 24 of the angioplasty catheter 191 was at the proper location the balloon 195 would be deployed to open the artery. Finally, the electrical activity of the site would be reviewed to determine whether the underlying tissue 125 was now receiving a proper blood supply and thus was no longer electrically abnormal.

We claim:

1. A method for generating a time series electrogram, the method comprising the steps of:

a) placing an electrode array into a chamber of the heart and measuring potentials on said array creating measured potentials;

b) building a model of the chamber wall;

c) displaying the model of the chamber wall;

d) selecting a site on the displayed model of the chamber wall;

e) calculating the potential at the selected site over a period of time utilizing the measured potentials received by the electrode array; and f) displaying the calculated potentials as a wave form.

2. The method of claim 1, wherein the electrode array includes both passive and active electrodes.

3. The method of claim 1, further comprising the step of periodically updating the displayed wave form potential based upon further measured potentials.

4. The method of claim 1, wherein the step of building a model of the chamber wall includes the following substeps:

i) supplying an oscillating current to a first subset of electrodes in the electrode array;

ii) detecting the electric field associated with the oscillating current on a second subset of electrodes in the electrode array;

iii) determining the impedance present between the first and second subset of electrodes; and iv) using a physical distance relationship between the first and second subset of electrodes on the electrode array and an assumed impedance characteristic or resistance of blood and tissue to calculate a model of the chamber wall.

5. The method of claim 4, further comprising the steps of calculating the electrophysiology of the chamber wall and displaying the calculated electrophysiology on the displayed model of the chamber walls.

6. The method of claim 5, wherein the displayed wave form and the displayed electrophysiology are simultaneously displayed and updated over time.

7. The method of claim 5, wherein the step of calculating the electrophysiology of the chamber wall includes the following substeps:

i) measuring a voltage at non-powered electrodes in the electrode array presented to the electrodes by depolarization biopotentials of the heart;

ii) selecting locations on the chamber wall where potentials are to be measured;

iii) determining the potentials at the selected locations based upon the measured voltage; and iv) interpolating the potentials at intermediate locations based upon the potentials at the selected locations.

\* \* \* \* \*